(12) United States Patent
Bremner et al.

(10) Patent No.: US 7,814,907 B2
(45) Date of Patent: Oct. 19, 2010

(54) SYSTEM FOR SENSING THE DELIVERY OF GASES TO A PATIENT

(75) Inventors: Michael Brian Edward Bremner, Warkworth (NZ); Brett John Huddart, Auckland (NZ); Scott Robert Mackie, Auckland (NZ)

(73) Assignee: Fisher & Paykel Healthcare Limited (NZ)

( * ) Notice: Subject to any disclaimer, the term of this patent is extended or adjusted under 35 U.S.C. 154(b) by 546 days.

(21) Appl. No.: 10/533,411

(22) PCT Filed: Oct. 30, 2003

(86) PCT No.: PCT/NZ03/00244

§ 371 (c)(1),
(2), (4) Date: Oct. 17, 2005

(87) PCT Pub. No.: WO2004/039444

PCT Pub. Date: May 13, 2004

(65) Prior Publication Data

US 2006/0118113 A1 Jun. 8, 2006

(30) Foreign Application Priority Data

Nov. 1, 2002 (NZ) .................................... 522375

(51) Int. Cl.
*A61M 16/00* (2006.01)
*A61M 16/10* (2006.01)
*A61M 16/16* (2006.01)

(52) U.S. Cl. ........................ 128/205.23; 128/204.17; 128/203.26; 128/203.27; 128/204.18; 128/204.21; 128/205.25

(58) Field of Classification Search ............ 128/203.16, 128/203.17, 200.11, 200.24, 204.17, 204.18, 128/204.21, 204.22, 204.26, 205.27, 913
See application file for complete search history.

(56) References Cited

U.S. PATENT DOCUMENTS 4,288,396 A * 9/1981 Ottestad .................... 261/128

(Continued)

FOREIGN PATENT DOCUMENTS

AU 1486395 9/1995

(Continued)

OTHER PUBLICATIONS

Webster's New World Dictionary, Third College Edition, 1988, p. 655, definition of housing.*

*Primary Examiner*—Justine R Yu
*Assistant Examiner*—Clinton Ostrup
(74) *Attorney, Agent, or Firm*—Clark Hill PLC (57) ABSTRACT

The present invention provides improvements in the feedback and control systems employed in the field of ventilation therapy. In particular, a system for delivering a supply of gases to a patient is described which incorporates a detachable cartridge or open tubular section (22) used to house a mechanism (11) which senses the humidity, temperature, flow and other attributes of the flowing gas. Information obtained from the sensor may be used to provide feedback to a controller (9) which controls the humidification mechanism in order to provide optimally humidified gases to a patient (1). It will be appreciated that the feedback and control system as described in the preferred embodiment of the present invention can be used in respiratory care generally or with a ventilator.

20 Claims, 6 Drawing Sheets

U.S. PATENT DOCUMENTS

| | | | |
|---|---|---|---|
| 4,366,821 A * | 1/1983 | Wittmaier et al. | 600/532 |
| 4,525,937 A * | 7/1985 | Strandberg et al. | 34/550 |
| 5,291,897 A * | 3/1994 | Gastrin et al. | 600/529 |
| 5,367,604 A * | 11/1994 | Murray | 392/394 |
| 5,411,474 A | 5/1995 | Ott et al. | |
| 5,443,075 A * | 8/1995 | Holscher | 600/538 |
| 5,640,951 A | 6/1997 | Huddart et al. | |
| 5,873,361 A * | 2/1999 | Hakala | 128/204.23 |
| 5,925,831 A * | 7/1999 | Storsved | 73/861.52 |
| 6,000,397 A * | 12/1999 | Skog | 128/204.22 |
| 6,039,696 A * | 3/2000 | Bell | 600/532 |
| 6,050,260 A | 4/2000 | Daniell et al. | |
| 6,068,609 A * | 5/2000 | Ott et al. | 604/26 |
| 6,102,037 A | 8/2000 | Koch | |
| 6,138,674 A * | 10/2000 | Gull et al. | 128/204.21 |
| 6,272,933 B1 * | 8/2001 | Gradon et al. | 73/861 |
| 6,308,706 B1 * | 10/2001 | Lammers et al. | 128/204.22 |
| 6,349,722 B1 * | 2/2002 | Gradon et al. | 128/203.17 |
| 7,066,902 B1 * | 6/2006 | Ott et al. | 604/23 |
| 2002/0078733 A1 * | 6/2002 | Seakins et al. | 73/29.02 |
| 2002/0100320 A1 | 8/2002 | Smith et al. | |
| 2004/0069307 A1 * | 4/2004 | Rich et al. | 128/207.14 |
| 2006/0137445 A1 * | 6/2006 | Smith et al. | 73/204.22 |

FOREIGN PATENT DOCUMENTS

| | | | |
|---|---|---|---|
| DE | 3709122 A * | 9/1988 | |
| EP | 1329240 | 7/2003 | |
| EP | 1329240 A1 * | 7/2003 | |
| GB | 2010097 A * | 6/1979 | |
| GB | 2127299 A * | 4/1984 | |
| GB | 2190000 A * | 11/1987 | |
| GB | 2297914 | 8/1996 | |
| JP | 9-234247 | 9/1997 | |
| WO | WO 01/13981 | 3/2001 | |
| WO | 02/32486 | 4/2002 | |
| WO | 02/085438 | 10/2002 | |
| WO | WO 03/018096 | 3/2003 | |

* cited by examiner

SYSTEM FOR SENSING THE DELIVERY OF GASES TO A PATIENT

TECHNICAL FIELD

This invention relates to humidity, temperature and flow sensing and particularly but not solely to the supply of optimally humidified gases to assist a patient's breathing for ventilation purposes, or for the supply of gases for other medical procedures, such as laparoscopic, endoscopic or ophthalmic procedures.

BACKGROUND ART

A number of methods are known in the art for assisting a patient's breathing. Continuous Positive Airway pressure or CPAP involves the administration of air under pressure to a patient, usually by a nasal mask. It is used in the treatment of snoring and Obstructive Sleep Apnea (OSA), a condition characterised by repetitive collapse of the upper airway during inspiration. Positive pressure splints the upper airway open, preventing its collapse. Treatment of OSA with nasal CPAP has proven to be both effective and safe, but CPAP is difficult to use and the majority of patients experience significant side effects, particularly in the early stages of treatment.

Upper airway symptoms adversely affect treatment with CPAP. Mucosal drying is uncomfortable and may awaken patients during the night. Rebound nasal congestion commonly occurs during the following day, simulating a viral infection. If untreated, upper airway symptoms adversely affect rates of CPAP use.

Increases in nasal resistance may affect the level of CPAP treatment delivered to the pharynx, and reduce the effectiveness of treatment. An individual pressure is determined for each patient using CPAP and this pressure is set at the mask. Changes in nasal resistance affect pressure delivered to the pharynx and if the changes are of sufficient magnitude there may be recurrence of snoring or airway collapse.

Such symptoms can also occur in a hospital environment where a patient is on a respirator. Typically in such situations the patient is intubated. Therefore the throat tissue may become irritated and inflamed causing both distress to the patient and possible further respiratory problems.

A number of methods may be employed to treat such upper airway symptoms, including pharmacological agents to reduce nasal disease, or heating the bedroom. One most commonly employed method is humidification of the inspired air using an in line humidifier. Two types of humidifier are currently used. Cold pass-over humidifiers rely on humidifying the air through exposure to a large surface area of water. While they are cheap, the humidity output is low at high flows, typically 2 to 4 mg/L absolute humidity at flows above 25 L/min. The output is insufficient to prevent mucosal drying. Heated water bath humidifiers are more efficient and produce high levels of humidity even at high flow rates. They are effective at preventing upper airway mucosal drying, prevent increases in nasal resistance, and are the most reliable means of treating upper airway symptoms.

Any of these active systems will have, to some degree or other, condensation (or rain out) in the tubing connecting the humidifier to the patient. The degree of condensation is strongly dependent on the ambient temperature, being much greater for greater differences between the ambient temperature and the gas temperature. The formation of large quantities of water in the breathing tubing causes considerable inconvenience to the patient, may accelerate cooling of the gas, may eventually occlude the tubing, or may be expelled into the patient. Also, the patient may experience discomfort, when breathing gases are delivered at temperatures widely divergent from that of the ambient temperature. Excessive condensation also results in inefficient usage of the water in the humidifying chamber.

In a hospital environment, where the ambient temperature of the atmosphere within the hospital environment is controlled by air conditioning for example, the required temperature for the humidified gases supplied by the apparatus may be controlled within set temperature parameters that are sufficiently close to the ambient temperature to prevent condensation within the conduit. However it is still necessary to have good control over the temperature and humidity of gases as they are actually supplied to the patient.

In the home care environment in which a user requires to use humidifying apparatus at home, the range of ambient and gas temperatures may well exceed that of the hospital environment. In the home care environment, the user will usually wear a facemask that is connected to the end of a gases supply conduit which may be in fluid communication with a humidifier for the treatment of breathing and sleep apnea disorders and/or in conjunction with ventilators or CPAP devices. In addition, non-active humidifiers are commonly employed utilising the known pass over humidification technique.

For medical procedures where a patient's cavity is inflated for surgery, such as with laparoscopic or endoscopic surgery, it is important that gases entering the cavity are humid and at body temperature so as not to cause drying of the cavity tissues and to improve the recovery time of the patient.

In U.S. Pat. No. 5,640,951 issued to Fisher and Paykel Limited, a heated conduit for a humidified breathing assistance apparatus is disclosed which includes a temperature probe at the end of a heated conduit. By heating the conduit the problems relating to condensation in the conduit may be overcome. However in order to implement closed loop control over the temperature of the supplied gases (and therefore the power input to the conduit heating element 21), it is necessary to measure the temperature as close to the point at which it is supplied as possible. The temperature probe and its associated wiring included for this purpose make the attachment to the facemask or intubated patient bulky and therefore more uncomfortable for the patient. Also for other medical procedures the probes and associated wiring also result in bulky attachments at the operation entry point causing obstructions to the surgeon or pressure sores around the point of entry.

WO01/13981 of Fisher & Paykel Limited discloses a breathing assistance apparatus adapted to deliver humidified gases at a desired level of humidity to a patient, including a humidifier and a heated conduit. The humidifier includes a controller, which determines a parameter of gas flow rate and then the required power input to the humidifier to deliver the gases to the patient at the required patient humidity. In a second embodiment, a conduit heating element is provided and the controller determines whether it has been correctly connected to the control circuitry. The heater plate of the humidifier is controlled to a particular temperature (set point) or the heater plate power is controlled through estimation or measurement of flow and/or ambient temperature. The heating element within the conduit is controlled by controlling the power to the heater through measurement or estimation of flow and ambient temperature. This eliminates the need for probes or external sensors. The blower or fan of this apparatus is pressure controlled for the purpose of treating CPAP. With this system the humidity of the gases supplied to the patient is not so accurate, particularly at high flows.

It is an object of the present invention to provide a system for delivering gases to a patient and sensing means which go some way to overcoming the abovementioned disadvantages or which at least provides the public or industry with a useful choice.

DISCLOSURE OF INVENTION

Accordingly, the present invention consists in a system for delivering a supply of gases to a patient comprising:

a gases supply providing a flow of gases, a humidifier receiving said flow of gases from said gases supply and capable of humidifying said flow of gases up to a level of humidity prior to delivery to said patient, a conduit conveying said flow of gases from said humidifier to said patient, a sensor to sense the humidity, temperature or flow rate of said flow of gases, said sensor in use being releasably coupled in line between said humidifier and said conduit, and a filter material such that said sensor is exposed to said flow of gases through said filter material.

In a second aspect the present invention consists in a sensing device to sense humidity, temperature or flow rate of a flow of gases after said flow of gases have been humidified by a humidifier and providing feedback to a controller which controls said humidifier, said sensing device comprising:

a cartridge or open tubular section, a sensor, and a filter material, wherein said cartridge or open tubular section is coupled to said sensor, such that said sensor is exposed to said flow of gases through said cartridge or open tubular section through said filter material.

In a further aspect the present invention consists in a system for delivering a supply of gases to a patient including a sensing means as described above.

To those skilled in the art to which the present invention relates, many changes in construction and widely differing embodiments and applications of the invention will suggest themselves without departing from the scope of the invention as defined in the appended claims. The disclosures and descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings in which.

BEST MODES FOR CARRYING OUT THE INVENTION

The present invention provides a system for the delivery of gases to a patient and more particularly to a sensing means capable of sensing temperature or humidity downstream of a humidifier chamber, that is, on the wet-side of the system. The sensing means or part of the sensing means, for example, the sensor housing or cartridge, is capable of being removed and cleaned, for example in any autoclave, or alternatively disposed of and replaced. So, cross-contamination between patients on second or subsequent use of the sensing means or sensor is not possible. The sensing means of the present invention allows for the protection of a sensor from wet-side contaminants by means of a filter material. Therefore, wet-side contaminants are prevented from affecting the sensor's performance.

Also, the sensing means allows for accurate sensing after the humidifier, thus creating effective inputs for feedback control of the humidifier and more specifically the heating and humidification of gases passing through the humidifier.

The sensing means of the present invention may be used for various applications such as laparoscopic, ophthalmic or other surgical procedures, tracheostomised patients, and trans-tracheal insufflation, in particular, in systems that provide a humidified gas supply.

The present invention provides a sensing means in a system where the flow of gases passes in sequence through a gases supply means or flow driver (such as, a blower, fan, compressor or insufflator), humidification means, including a humidification chamber, and then heated delivery circuit. Typical blower humidifier combinations have been designed for the treatment of obstructive sleep apnoea and are pressure-controlled devices. They are also typically designed to be used as stand-alone blowers or in combination with a simple humidifier. These therefore typically deliver low levels of humidity i.e. 28 to 32 mg/L. The sensing means of the present invention is intended to be used with a gases supply means and humidification means to deliver body temperature saturated gases, that is, 37° C. and containing 44 mg of water vapour per liter, to a patient over a range of flows, for example, flow that would typically be used to provide for a patient's inspiratory flow requirements (i.e. peak inspiratory flow).

Figure 1:
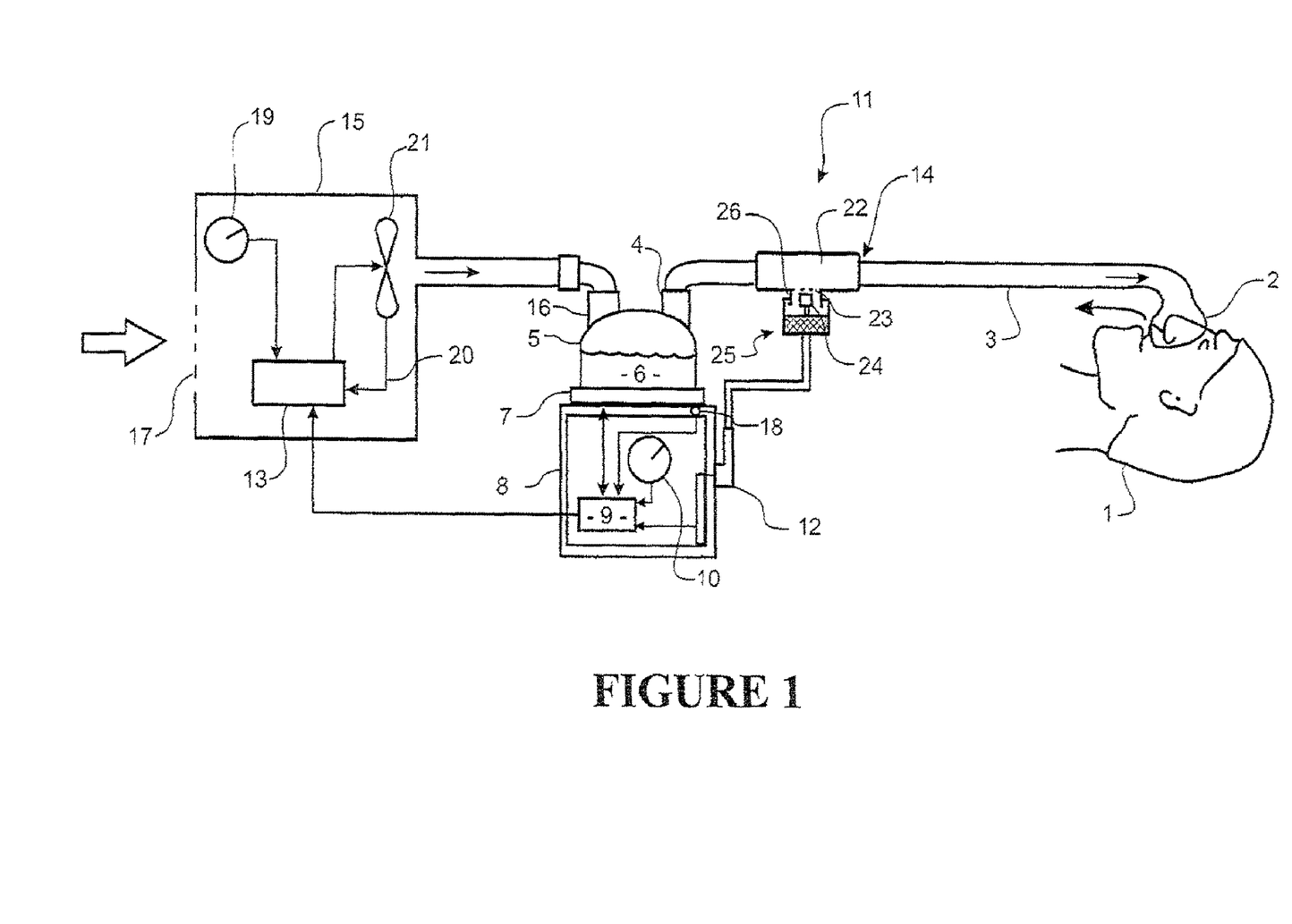
FIG. 1 is a schematic of the system for delivering gases to a patient and sensing means of the present invention.

With reference to FIG. 1 a humidified positive pressure ventilation system is shown that may utilise the sensing means of the present invention. A patient 1 is receiving humidified and pressurised gases through a nasal mask 2 connected to a humidified gases transportation means or inspiratory conduit 3. It should be understood that delivery systems could also be VPAP (Variable Positive Airway Pressure) and BiPAP (Bi-level Positive Airway Pressure) or numerous other forms of respiratory therapy. The inspiratory conduit 3 is connected to the outlet 4 of a humidification chamber 5, which contains a volume of water 6. The inspiratory conduit 3 may contain heating means or heater wires (not shown), which heat the walls of the conduit to reduce condensation of humidified gases within the conduit. The humidification chamber 5 is preferably formed from a plastics material and may have a highly heat conductive base (for example an aluminium base) which is in direct contact with a heater plate 7 of humidifier 8. The humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller also receives input from the sensing means 11 through connector 12 and heater plate temperature sensor 13. In response to a user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16.

Blower 15 is provided with variable pressure regulating means or variable speed fan 21, which draws air or other gases through blower inlet 17. The speed of variable speed fan 21 is controlled by electronic controller 18 (or alternatively the function of controller 18 could carried out by controller 9) in response to inputs from controller 9 and a user set predetermined required value (preset value) of pressure or fan speed via dial 19.

Figure 9:
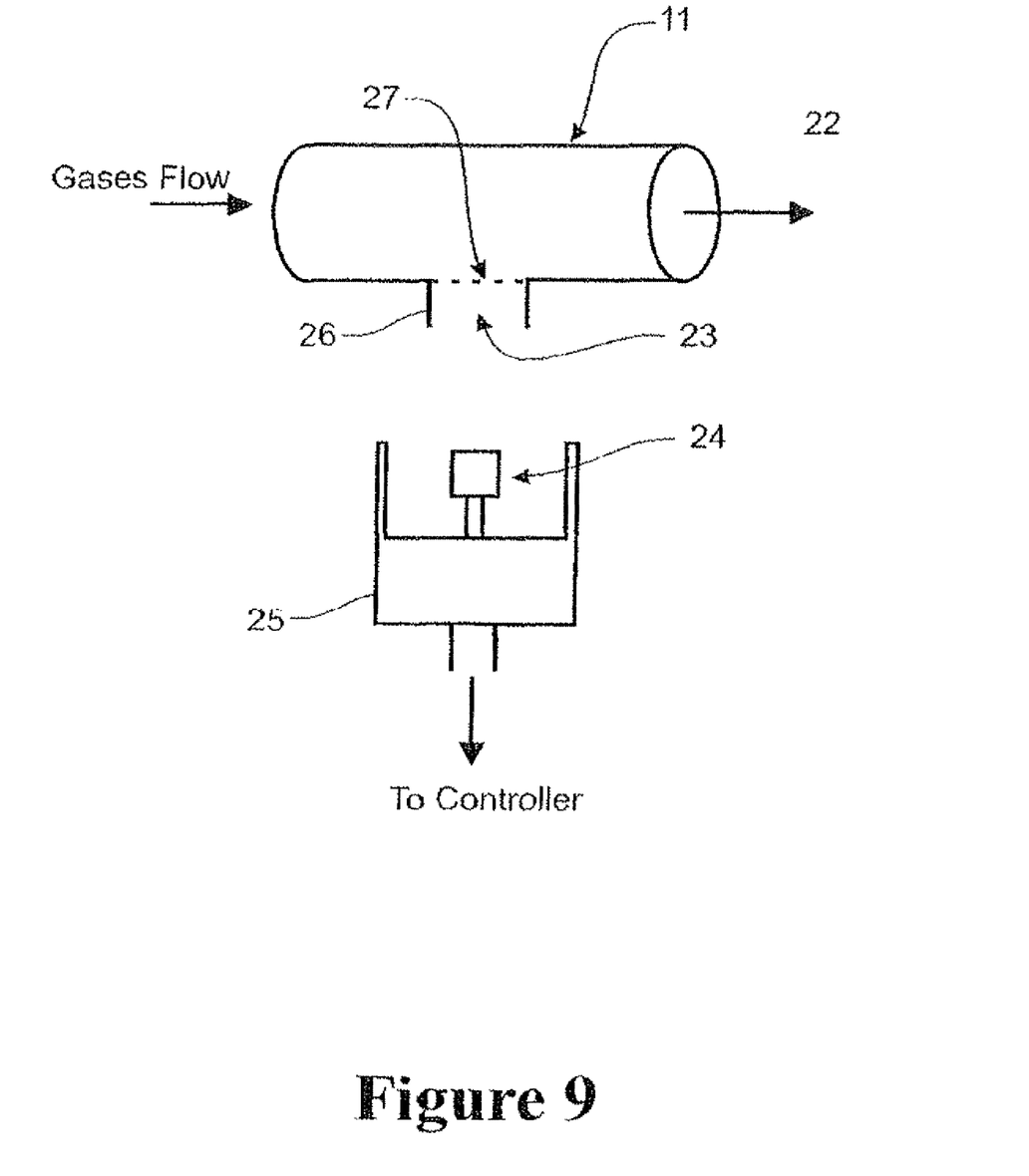
FIG. 9 is an exploded view of the sensing means of FIG. 1.
Figure 10:
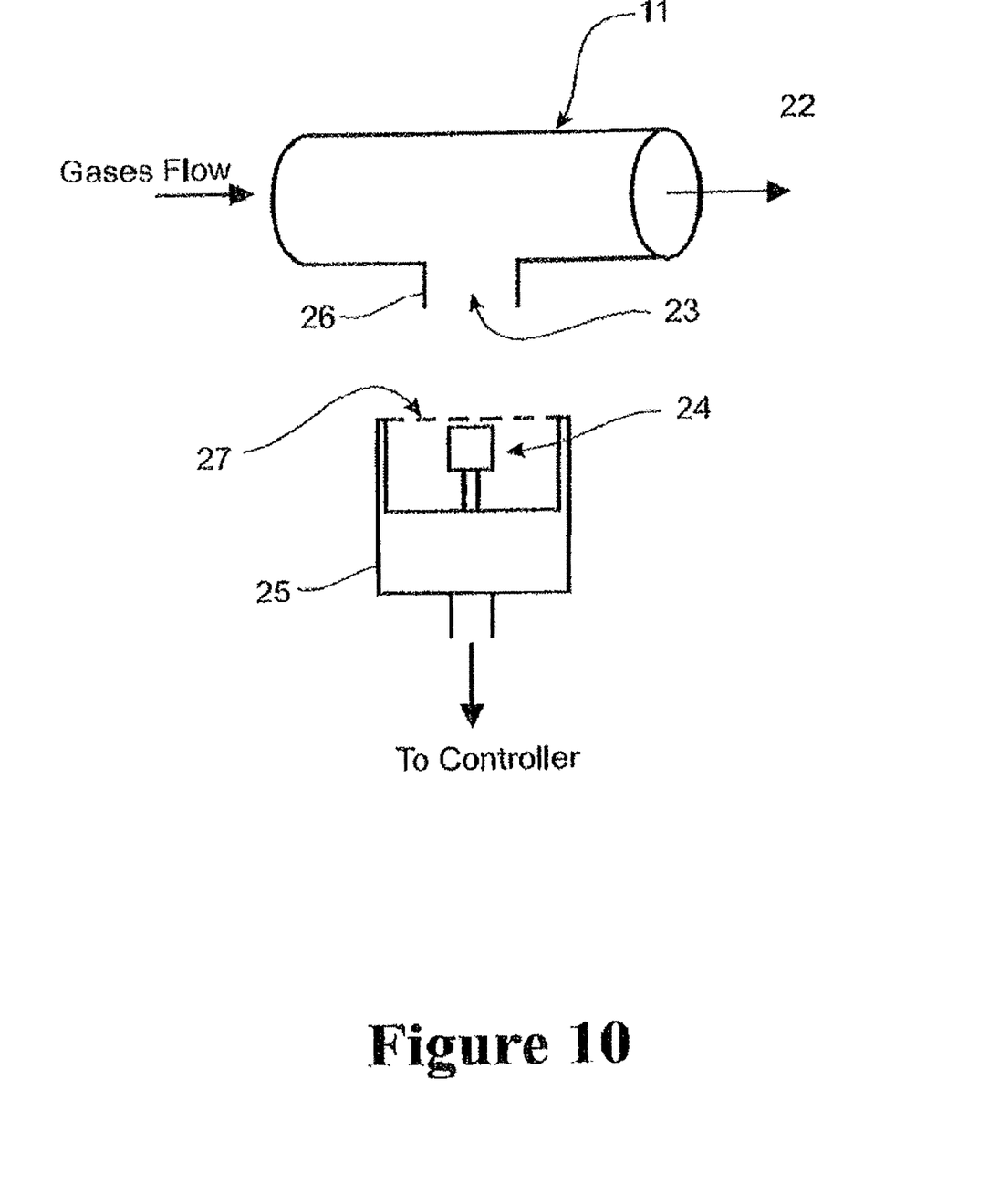
FIG. 10 is an exploded view of an alternative sensing means.

Referring now to FIGS. 1 and 9, in the preferred form the sensing means 11 is a removable cartridge or a section of open tubing 22 that is connected between the humidifier outlet 4 and one end 14 of the inspiratory conduit 3. In particular one side of the cartridge or open tubular section 22 is connected to the outlet 4 of the humidification chamber 5 and the other side of the cartridge or open tubular section 22 is connected to the inspiratory conduit 3. Preferably the connections described above are made by way of a friction fitting, bayonet fitting, snap fitting, threadable connection, or other appropriate fastening means, known in the art of conduits and tubing.

The tubing is made from an appropriate plastics or metal material. A cavity 23 is formed in the side of the tubing 22 and in the preferred form covered with a filter material that provides for the filtration of the gases stream passing through the section of tubing 22. The filter material may be integrally formed with the tubing 22 or may be attached after the tubing is formed, for example by gluing or any other appropriate fastening means. The filter material is preferably a semi-permeable, breathable or hydrophilic material; such as a hydrophilic polyester block copolymer formed into a homogeneous flat film, for example, SYMPATEX™, but may be any one of the following; monolithic film, microporous media or could be an electrostatic filter, or other appropriate material.

The filter material is adapted to be fitted over the cavity 23 and is capable of preventing dust, mist, bacteria or viruses from passing directly from the gases stream to the sensor 24 contained within a sensor housing 25, but allows for clean humidified gases to pass through the cavity 23 and filter material into a sensor housing 25. If the sensor and/or housing are to be reused, as there is no build up of contaminants on the sensor 24, and also as the housing and sensor 24 are more easily cleaned, second and subsequent use of the sensing means ensure no contamination occurs between patients.

In some forms of the present invention the sensor 24 is removable from the housing 25 and section of conduit. In these instances the housing and section of conduit, being made from low cost materials, can be disposed of, and the contaminant free sensor reused.

The sensor housing 25 is connected to the section of tubing 22 at a port 26 that surrounds the cavity 23. The connection between the port 26 and sensor housing 25 is such that an airtight seal is provided between the housing 25 and port 26. This connection may be made by way of a thread, snap fitting, bayonet type fitting, rubber-silicon sleeve/boot fitting or any other appropriate fitting. The sensor housing 25 holds the sensor 24 within the port 26 in such a manner to expose it to any gases filtering through into the housing. This housing 25 is preferably made from a plastics type material, but may be made from any other appropriate material, and the sensor 24 is attached within the housing either by being integrally moulded with the housing or by other appropriate fastening or attaching means.

Measurements taken from the sensor 24 are passed through wiring or the like to the connector 12 and to the controller 9. Continual sensing of the humidity of the gases passing through the tubing section 22 is achieved and sensed measurements of humidity, temperature and/or flow are fed back to the controller and more accurate control of the gases humidity, temperature and/or flow can be achieved. This is because the controller can adjust the temperature of the heater plate on the humidification means to cause more or less water within the chamber to be vaporised and/or the gases temperature increased or reduced. In the case of gases flow, to increase the flow rate, the controller may cause the flow rate from the gases supply to be increased or decreased.

In other forms of the sensing means of the present invention the cavity 23 may not be covered with the filter material as described above, but the end of the sensor housing 25 may be covered with such a material.

Figure 2:
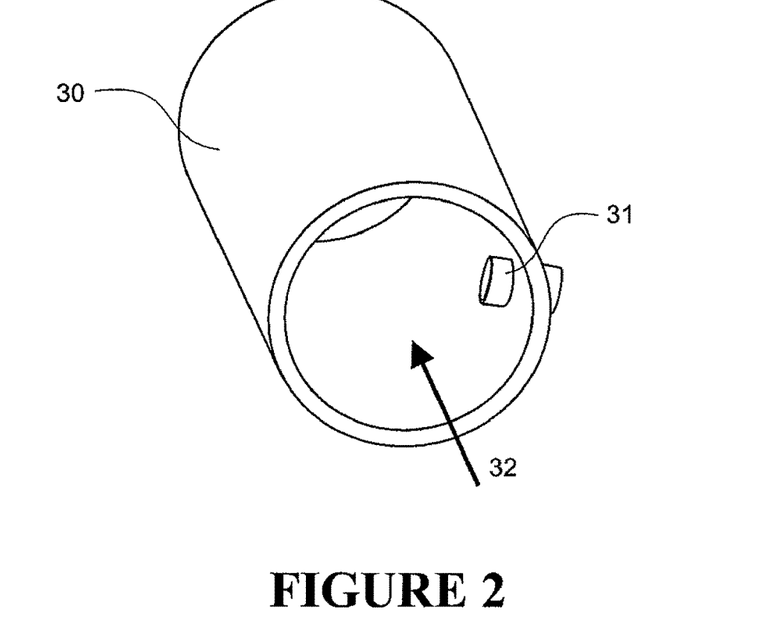
FIG. 2 is perspective view of a first form of the sensing means of the present invention.

Referring now to FIG. 2, which shows an illustration of another preferred form of the sensing apparatus of the present invention. The tubing 30 has a cavity in which the sensor housing 31 extends through and is adapted to be fixed in an airtight manner within the cavity. The end of the sensor housing 31 is within the gases flow (arrow 32) through the tubing 30 and is exposed to the gases flow. The end exposed to the gases flow is formed of the filter material as described above. Thus in this form, the sensor housing assembly is contained partially within the flow tube and partially in the environment external to the flow tube. Other forms of the sensor housing are described below in relation to FIGS. 4 to 8.

Figure 3:
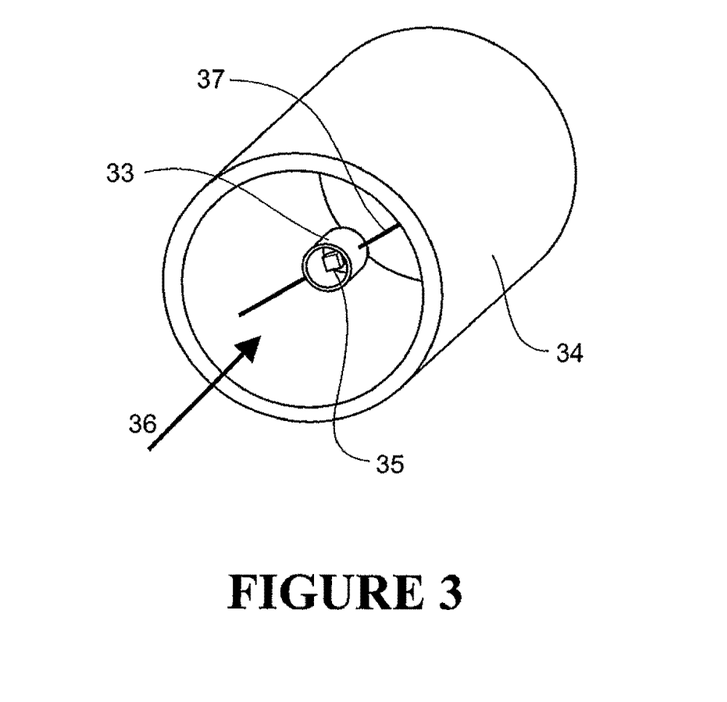
FIG. 3 is a perspective view of a second form of the sensing means of the present invention.

In other forms of the present invention, such as that shown in FIG. 3, a sensor housing forming part of the sensing apparatus may be contained or suspended wholly within a section of tubing 34 (similar to that described above in relation to FIG. 1), and a sensor 35 contained within the sensor housing 33. The sensor housing is held within the tubing 34 on integrally moulded arms 37, but other appropriate means to hold the housing suspended within the tubing are envisaged, such as a clip fitting that snap fits the housing to the inner wall of the conduit. Wiring (not shown) is attached to the sensor and wires run out of the housing, via the wires themselves or pins, that are connected to additional wiring and then to the controller 9.

Figure 4:
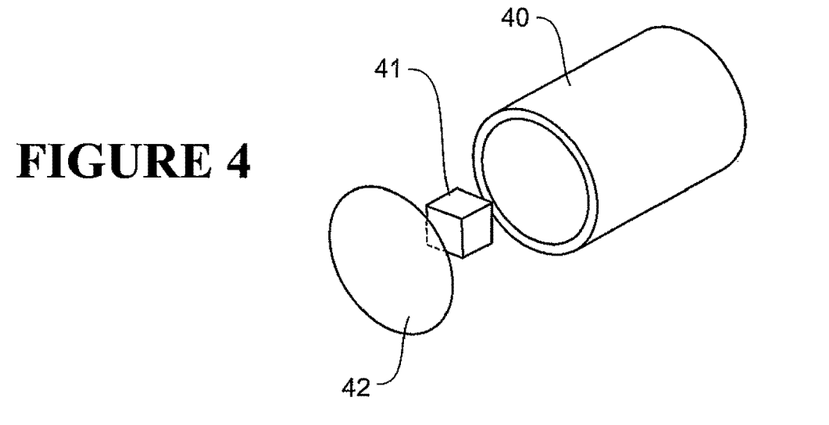
FIG. 4 is an exploded view of a first form of the sensor housing of the sensor means of the present invention.

The sensor housing as described in any of the forms of the sensing means above may be one of a number of forms itself, FIGS. 4 to 8 give some examples of some of these forms. Firstly, FIG. 4 shows an exploded view of a sensor housing 40. When assembled the sensor 41 is located within the sensor housing 40. A filter material 42 forms one end of the sensor housing 40 and the other end of the tubular housing 40 remains open. Thus, the sensor housing 40 and filtration material 42 partially encapsulate the sensor 41. Note must be made that the housing in the form of FIG. 4 would not be suitable for use with the sensing means configuration of FIG.

3, as gases flowing through the sensing means of FIG. 3 could access the sensor through the open housing of FIG. 4.

Figure 5:
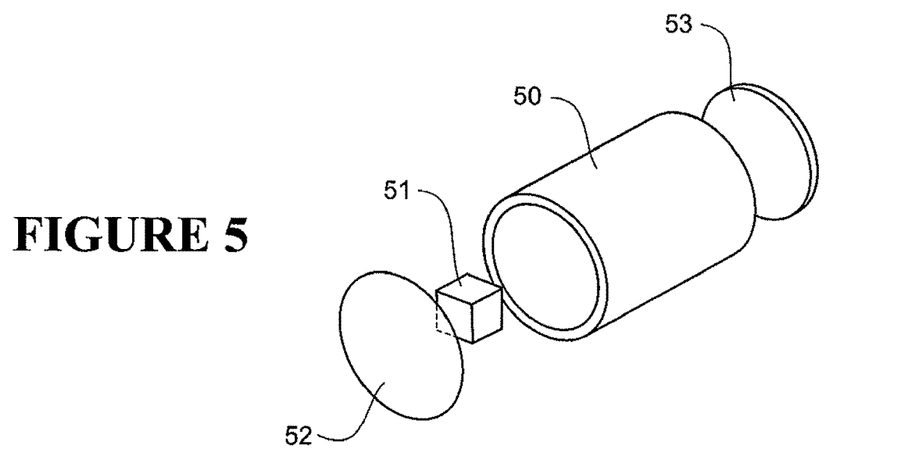
FIG. 5 is an exploded view of a second form of the sensor housing of the sensor means of the present invention.
Figure 6:
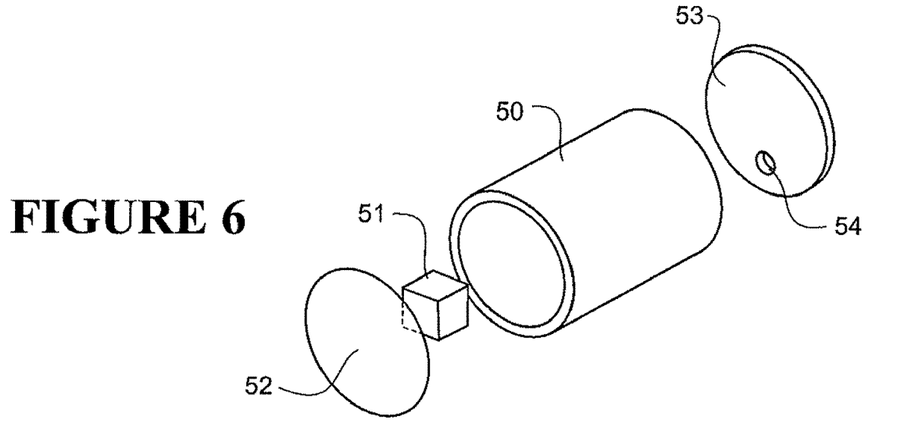
FIG. 6 is an exploded view of a third form of the sensor housing of the sensor means of the present invention.

FIG. 5 shows an exploded view of another example of a form of a sensor housing. The filter material 52 forms one end of the sensor housing 50 and the other end 53 of the sensor housing is closed off so that the sensor 51 is fully encapsulated within the housing. Both the housing 50 and end 53 are formed of the same material, such as a plastics material. In another form, such as that in FIG. 6, the other end of the housing 53 has a vent hole 54. The vent hole 54 has the purpose of enabling the environmental conditions in the housing to reach equilibrium faster with the outside of the housing, to minimise lag in sensor response in returning to ambient conditions. Again, connections from the sensor to the controller are not shown, but would be made by way or wiring or the like.

Figure 7:
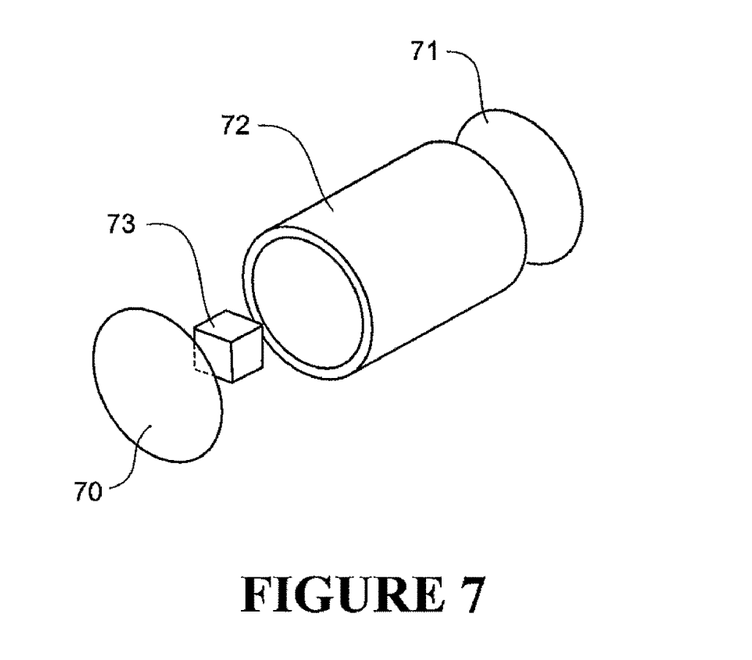
FIG. 7 is an exploded view of a fourth form of the sensor housing of the sensor means of the present invention.

In yet other forms, such as that of FIG. 7, both ends 70 and 71 of the housing 72 may be formed from the filter material and the sensor 73 is fully encapsulated within the housing 72.

Figure 8:
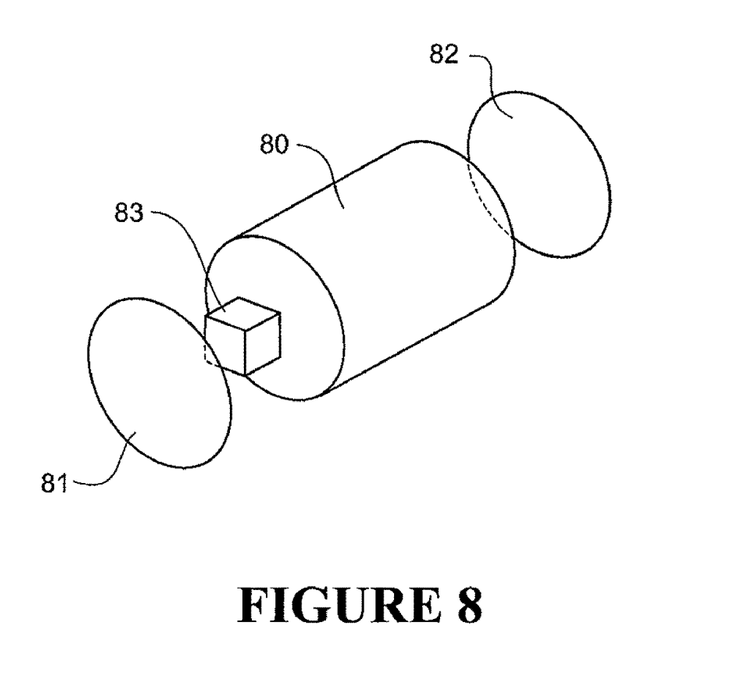
FIG. 8 is an exploded view of a fifth form of the sensor housing of the sensor means of the present invention.

As a final example, FIG. 8 shows a housing 80 where the housing 80 and housing ends 81 and 82 are made of the filter material. The filter material is a semi-permeable or hydrophilic material that allows gases through but not condensation, viruses, bacteria or other similar contaminants that may affect the sensors operation or damage the sensor.

In other forms of the sensing apparatus of the present invention the sensor housing (of one or other of the forms disclosed above) may optionally have a heating element. Often when sensors are exposed to condensate they can become saturated and may begin to sense inaccurately. By heating the inside of the housing and sensor, the sensors performance or response can be optimised. A heating element may be housed within the sensor housing in a manner such that the heating element is physically detached from the sensor and which provides indirect heating of the sensor. In other forms the heating element may be physically attached to the sensor providing direct heating of the sensor. In yet another form the heating element may be attached to the outside of the sensor housing providing for indirect heating of the sensor via heating of the sensor housing.

The invention claimed is:

1. A system for delivering a supply of gases to a patient comprising:
    a gases supply providing a flow of gases,
    a humidifier receiving said flow of gases from said gases supply and capable of humidifying said flow of gases up to a level of humidity prior to delivery to said patient,
    a conduit conveying said flow of gases from said humidifier to said patient,
    a sensing device to sense the humidity, temperature or flow rate of said flow of gases after said flow of gases have been humidified by said humidifier, said sensing device comprising:
        a cartridge or open tubular section having a port,
        a sensor,
        a housing removably containing said sensor,
        a filter attached to said housing, and
    wherein the cartridge or open tubular section is removably coupled, in use, in line between said humidifier and said conduit, the housing being removably coupled to said port of said cartridge or open tubular section, in use said housing being sealably connected to the port such that said sensor is exposed to said flow of gases through said cartridge or open tubular section, and the filter being located such that said sensor is exposed to a portion of said flow of gases passing through said filter only, with a significant portion of the flow of gases passing from the humidifier to the conduit without passing through the filter material,
    the filter and housing preventing contamination passing from the flow of gases to the sensor, the sensor being removable from the housing for subsequent reuse, the functionality of said sensor being intact after removal from the housing.

2. A system according to claim 1 wherein said humidifier includes a humidification chamber adapted to receive a volume of water and a water heater to heat said water, said flow of gases passing through said humidification chamber, through a gases inlet and out a gases outlet, and evaporating said water, said flow of gases thereby being humidified.

3. A system according to claim 2 wherein said humidifier includes a controller to control said water heater and the level of humidity or temperature of said flow of gases.

4. A system according to claim 3 wherein said sensor is connected to said controller and conveys a sensed level of humidification of said flow of gases to said controller, said controller controlling said water heater to alter said sensed level of humidification of said flow of gases to a predetermined humidification level.

5. A system according to claim 4 wherein said predetermined humidification level is such that said patient receives said flow of gases at 37° C. and containing 44 mg of water vapour per liter.

6. A system according to claim 2 wherein in use, connections are formed between one side of said cartridge or open tubular section and said outlet of said humidifier and the other side of said cartridge or open tubular section and said conduit.

7. A system according to claim 6, wherein said connections are one of a friction fitting, bayonet fitting, snap fitting or threadable connection.

8. A system according to claim 1, wherein said housing extends through or resides within said cartridge or open tubular section and at least part of said filter is exposed to said flow of gases.

9. A system according to claim 1, wherein said filter is a semi-permeable or hydrophilic material.

10. A system according to claim 1, wherein said filter is monolithic film, microporous media or electrostatic filter.

11. A system according to claim 1, further including a sensor heater to provide heat to said sensor.

12. A system according to claim 11, wherein said sensor heater is contained within said housing.

13. A sensing device to sense humidity, temperature or flow rate of a flow of gases in a conduit after said flow of gases have been humidified by a humidifier and providing feedback to a controller which controls said humidifier, said sensing device comprising:
    a cartridge or open tubular section having a port,
    a sensor,
    a housing removably containing said sensor, and
    a filter attached to said housing, and
    wherein said cartridge or open tubular section is removably coupled, in use, in line between the humidifier and the conduit, the housing being removably coupled to said port of said cartridge or open tubular section, in use said housing being sealably connected to the port such that said sensor is exposed to said flow of gases through said cartridge or open tubular section,
    said filter being located such that the sensor is exposed to a portion of the flow of gases passing through the filter only, with a significant portion of the flow of gases passing from the humidifier to the conduit without passing through the filter, the filter and housing preventing contamination passing from the flow of gases to the sensor, the sensor being removable from the housing for subsequent reuse, the functionality of said sensor being intact after removal from the housing.

14. A sensing device according to claim 13 wherein said housing extends through or resides within said cartridge or open tubular section and at least part of said filter is exposed to said flow of gases.

15. A sensing device according to claim 13 wherein said filter is a semi-permeable or hydrophilic material.

16. A sensing device according to claim 13 wherein said filter is monolithic film, microporous media or electrostatic filter.

17. A sensing device according to claim 13 further including a heater to provide heat to said sensor.

18. A sensing device according to claim 17, wherein said sensor heater is contained in said housing.

19. A sensing device according to claim 13, wherein in use, connections are formed between one side of said cartridge or open tubular section and an outlet of said humidifier and the other side of said cartridge or open tubular section and said conduit.

20. A sensing device according to claim 19, wherein said connections are one of a friction fitting, bayonet fitting, snap fitting or threadable connection.

* * * * *